United States Patent [19]

Piorr et al.

[11] Patent Number: 4,792,419

[45] Date of Patent: Dec. 20, 1988

[54] ETHER SULFONATES

[75] Inventors: Robert Piorr, Ratingen-Hoesel; Alfred Meffert, Monheim, both of Fed. Rep. of Germany

[73] Assignee: Henkel Kommanditgesellschaft auf Aktien, Duesseldorf, Fed. Rep. of Germany

[21] Appl. No.: 644,482

[22] Filed: Aug. 24, 1984

[30] Foreign Application Priority Data

Sep. 1, 1983 [DE] Fed. Rep. of Germany ....... 3331513

[51] Int. Cl.$^4$ ............................................. C07C 143/02
[52] U.S. Cl. .............................. 260/513 R; 260/504 R
[58] Field of Search ............ 260/504 R, 513 R, 513 T

[56] References Cited

U.S. PATENT DOCUMENTS 1,985,747 12/1934 Steindorff et al. ................. 260/151

FOREIGN PATENT DOCUMENTS 1530076 5/1968 France ............................ 260/513 T
5233096 7/1969 Japan ............................... 260/513 T

*Primary Examiner*—Alan Siegel
*Attorney, Agent, or Firm*—Ernest G. Szoke; Henry E. Millson, Jr.; Real J. Grandmaison

[57] ABSTRACT

Ether sulfonates are produced by reacting a $C_{10}$–$C_{20}$ fatty alkyl $C_1$–$C_6$ lower alkyl ether or a fatty alkyl (polyoxyalkyl) lower alkyl ether corresponding to the following formula $$R-O-(C_nH_{2n}O)_x-R^1 \qquad (I)$$ ps in which R is an oleyl, palmitoleyl, or linoleyl radical, or mixtures thereof, n is an integer of from 2 to 4, x is an integer of from 0 to 30, and $R^1$ is a saturated $C_1$–$C_6$ lower alkyl radical, with sulfur trioxide, contacting the sulfonate with aqueous alkali metal hydroxide solution and heating the solution until the sultones formed have been hydrolyzed.

11 Claims, No Drawings

ETHER SULFONATES

BACKGROUND OF THE INVENTION

1. Field of the Invention

This invention relates to a process for the production of ether sulfonates. The invention also relates to the ether sulfonates obtained by the process.

2. Description of the Relevant Art

Of the numerous groups of anionic surfactants, those containing an $SO_3^\ominus$-group as a water-solubilizing group are of the greatest commercial significance. Within that group, a distinction is drawn between sulfate surfactants and sulfonate surfactants.

The sulfate surfactants are semiester salts of sulfuric acid. Of these salts, alkyl ether sulfates are of particular importance because, by virtue of the glycol ether groups in the molecule, they show very high solubility in water and, accordingly, are particularly suitable for use in the production of liquid detergents and cleaners.

One disadvantage of alkyl ether sulfates is their inadequate resistance to hydrolysis which prevents them from being used of acidic cleaners.

Sulfonate surfactants are salts of alkyl sulfonic acids and are stable to hydrolysis, even in acidic medium. However, there are only a few, technically complex processes for the production of sulfonate surfactants which contain glycol ether groups to increase their solubility in water. Examples of known ether sulfonates are the alkyl glycol ether sulfonates known from U.S. Pat. No. 1,985,747, and the alkyl glyceryl ether sulfonates known from German Application Nos. 10 75 779 and 10 81 172.

DESCRIPTION OF THE INVENTION

An object of the present invention is to provide a process for the production of ether sulfonate surfactants which enables those surfactants to be produced from readily obtainable starting materials by a simple, continuous sulfonation process.

According to the invention, this object is achieved by a process for the production of ether sulfonates wherein at least one olefinically unsaturated $C_{10}$–$C_{20}$ fatty alkyl $C_1$–$C_6$ lower alkyl ether and/or an olefinically unsaturated fatty alkyl polyoxyalkyl lower alkyl ether corresponding to the following general formula

$$R-O(C_nH_{2n}O)_x-R^1 \qquad (I)$$

in which R represents an oleyl, palmitoleyl, or lineoleyl radical, n is an integer of from 2 to 4, x is an integer of from 0 to 30, and $R^1$ is a saturated $C_1$–$C_6$-lower alkyl radical, is reacted with sulfur trioxide, and the product of that reaction is contacted with, e.g. introduced into, an aqueous solution of from about 1 to about 1.2 moles of an alkali metal hydroxide per mole of $SO_3$ used above, and the solution is heated until the sultones formed thereby have been hydrolyzed. Mixtures of compounds of formula I wherein the R groups are predominantly oleyl, palmitoleyl, and linoleyl are advantageously used herein.

Ether sulfonates having particularly favorable performance properties are obtained when an unsaturated fatty alkyl polyoxyalkyl lower alkyl ether containing from 3 to 20 ethylene glycol ether groups, i.e. where n in general formula I has a value of 2 and x is a number of from 3 to 20, is used for sulfonation. The radical $R^1$ is preferably an n-butyl radical. The sulfonation of these unsaturated fatty alkyl (polyoxyalkyl) lower alkyl ethers is preferably carried out with gaseous sulfur trioxide at temperatures in the range of from about 20° to about 100° C. This reaction can be carried out continuously in standard reactors which are suitable for the sulfonation of fatty alcohols, fatty acid esters, alkylbenzene or olefins, preferably of the falling-film reactor type.

The sulfur trioxide is contacted with the unsaturated fatty alyl (polyoxyalkyl) lower alkyl ether after dilution with air or nitrogen, preferably in the form of a gas mixture containing about 1 to about 10% by volume of $SO_3$, preferably at a temperature in the range of from about 50° to about 70° C.

The crude sulfonation product is introduced into an aqueous solution of an alkali metal hydroxide which should contain the alkali metal hydroxide in a quantity of from about 1 to about 1.2 moles per mole of added sulfur trioxide. The slight excess of alkali metal hydroxide is used to neutralize the gaseous $SO_3$ dissolved in the sulfonation product and to maintain an excess of alkali which promotes the subsequent hydrolysis step. Sodium hydroxide is preferably used as the alkali metal hydroxide. The concentration of the alkali metal hydroxide solution is selected in such a way that the end product forms a solution of low viscosity.

In addition to unsaturated ether sulfonic acids, the reaction product also contains sultones. The formation of sultones in the sulfonation of olefinic double bonds is a known secondary reaction, which also occurs in the process of the invention. To convert the sultones, which are not wanted in the reaction product, into unsaturated sulfonates and hydroxysulfonates, the aqueous solution must be subjected to hydrolysis.

Hydrolysis is carried out by heating the solution until the sultones have been substantially completely destroyed. The time required depends upon the hydrolysis conditions. Where it is carried out, for example, at boiling temperature/normal pressure, hydrolysis takes from about 4 to about 6 hours; where it is carried out at a higher temperature and under pressure, it may be carried out much more quickly.

In the process of the invention, the ether sulfonates accumulate in the form of dark to light yellow aqueous, alkaline solutions. If desired, they can be bleached in known manner with hydrogen peroxide solution or with chlorine solution. The pH-value of the solutions can be adjusted to neutral using, for example, phosphoric acid, citric acid or lactic acid. For stabilization against bacterial contamination, it is advisable to add formaldehyde solution, p-hydroxybenzoate, sorbic acid or other known preservatives.

The starting compounds of formula I can be obtained by methods known from the literature. Their production starts from unsaturated fatty alcohols, for example oleyl alcohol or technical alcohol cuts consisting predominantly of oleyl alcohol, palmitoleyl alcohol and linoleyl alcohol. Small fractions of saturated alcohols, for example cetyl and stearyl alcohol, are acceptable therein, especially when the products of formula I produced therefrom by alkoxylation and etherification are themselves soluble in water. Suitable unsaturated alcohols can be obtained by the hydrogenation of oleic acid or technical oleic acids and are commercially available. Technical cetyl-oleyl and oleyl-linoleyl alcohol cuts having an iodine number in the range of from 70 to 130 are preferred.

The alkoxylation of unsaturated alcohols with ethylene oxide, propylene oxide, butylene oxide or mixtures of these alkylene oxides is a process which has long been carried out on an industrial scale. Mixtures of homologous alkoxylates, of which the average degree of alkoxylation corresponds to the quantity of added alkylene oxide, are obtained. The etherification of the terminal hydroxyl group of the unsaturated alcohols and/or their alkoxylates is carried out by methods likewise known from the literature. For example, it may be carried out by converting the alcohol or the alkoxylate with an alkali metal into the alcoholate, and reacting the alcoholate with an alkyl halide. In another process, the alcohol and the alkoxylate are reacted with an alkyl halide at elevated temperature in the presence of a finely powdered alkali metal hydroxide. Finally, the alkoxylate may be reacted with an alkyl chloride or alkyl bromide corresponding to the general formula $R^1$—Cl or $R^1$—Br, in which $R^1$ is a $C_1$–$C_6$ lower alkyl group, in the presence of an aqueous solution of NaOH or KOH in accordance with the process given in German Application No. 2 800 710.

The ether sulfonates obtained by the process of the invention show high surface activity and favorable performance properties as surfactants. Their wetting power with respect to glass, textiles and polyesters is particularly favorable. Their ready solubility in water and their satisfactory emulsifying power enables the products to be used both as commercial wetting agents and also in detergents and cleaners. Of particular importance is their resistance to hydrolysis, even in acidic medium, which considerably broadens their scope of application, for example by comparison with ether sulfates.

The invention is illustrated but not limited by the following Examples.

EXAMPLES

1. Oleyl alcohol-5EO-butylether sulfonate, Na-salt 886 g (approx. 1.6 moles) of the n-butylether of an adduct of 5 moles of ethylene oxide with a technical oleyl alcohol having an iodine number of 94 (HD-Ocenol® 92/96) were continuously reacted in a falling-film reactor at 60° C. with 187.8 g (approx. 2.35 moles) of gaseous $SO_3$ (driven out from oleum). After leaving the reactor, the reaction product was introduced into a solution of 98 g (2.45 moles) of NaOH in 1600 g of water. The solution obtained was boiled under reflux for 6 hours. A solution of the ether sulfonate characterized by the following data was obtained:
   Active substance (dry residue): 43.0% by weight
   Anionic surfactant (DGF-method H-III-10): 0.62 mval/g
   $Na_2SO_4$: 2.0% by weight
   Unsulfated (DGF-method G-III-6b): 6.0% by weight 2. Oleyl alcohol-10EO-butylether sulfonate Na-salt The n-butyl ether of an adduct of 10 moles of ethylene oxide with technical oleyl alcohol (HD-Ocenol® 92/96) was sulfonated in the same manner as set forth in Example 1. A sulfonate characterized by the following data was obtained:
   Active substance (dry residue): 33.8% by weight
   Anionic surfactant (DGF-method H-III-10): 0.39 mval/g
   $Na_2SO_4$: 1.9% by weight
   Unsulfated (DGF-method G-III-6b): 4.8% by weight 3. Oleyl alcohol-20EO-butylether sulfonate, Na-salt Starting from the n-butyl ether of an adduct of 20 moles of ethylene oxide with a technical oleyl alcohol (HD-Ocenol® 92/96), the corresponding sulfonate characterized by the following data was obtained by the process described in Example 1:
   Active substance (dry residue): 37.8% by weight
   Anionic surfactant (DGF-method H-III-10): 0.32 mval/g
   $Na_2SO_4$: 1.4% by weight
   Unsulfated (DGF-method G-III-6b): 6.6% by weight

What is claimed is:

1. An ether sulfonate which is the aqueous alkali metal hydroxide treated reaction product of sulfur trioxide and either an unsaturated $C_{10}$–$C_{20}$ fatty alkyl $C_1$–$C_6$ lower alkyl ether or an unsaturated fatty alkyl polyoxyalkyl lower alkyl ether of the formula $R$—$O(C_nH_{2n}O)_x$—$R^1$ (I) wherein R is an oleyl, palmitoleyl, or linoleyl group, n is an integer of from 2 to 4, x is an integer of from 0 to 30, and $R^1$ is a $C_1$–$C_6$ lower alkyl group.

2. An ether sulfonate in accordance with claim 1 wherein in the compound of formula I n is 2 and x is an integer of from 3 to 20.

3. An ether sulfonate in accordance with claim 1 wherein in the compound of formula I $R^1$ is the n-butyl group.

4. An ether sulfonate in accordance with claim 2 wherein in the compound of formula I $R^1$ is the n-butyl group.

5. An ether sulfonate in accordance with claim 1 wherein a mixture of compounds is present wherein the R groups in formula I are oleyl, palmitoleyl, and linoleyl.

6. The alkali metal salt of oleyl alcohol-5 EO-butylether sulfonate.

7. The alkali metal salt of oleyl alcohol-10 EO-butylether sulfonate.

8. The alkali metal salt of oleyl alcohol-20 EO-butylether sulfonate.

9. The compound of claim 6 wherein the alkali metal salt is the sodium salt.

10. The compound of claim 7 wherein the alkali metal salt is the sodium salt.

11. The compound of claim 8 wherein the alkali metal salt is the sodium salt.

* * * * *